(12) United States Patent
Wang et al.

(10) Patent No.: US 11,714,074 B2
(45) Date of Patent: *Aug. 1, 2023

(54) PARTICULATE MATTER MONITORING

(71) Applicant: International Business Machines Corporation, Armonk, NY (US)

(72) Inventors: Junsong Wang, Beijing (CN); Lingyun Wang, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 99 days.

This patent is subject to a terminal disclaimer.

(21) Appl. No.: 17/133,885

(22) Filed: Dec. 24, 2020

(65) Prior Publication Data

US 2021/0116431 A1 Apr. 22, 2021

Related U.S. Application Data

(63) Continuation of application No. 16/437,848, filed on Jun. 11, 2019, now Pat. No. 10,914,716, which is a
(Continued)

(51) Int. Cl.
*G01N 33/00* (2006.01)
*G01N 15/02* (2006.01)
(Continued)

(52) U.S. Cl.
CPC ..... *G01N 33/0027* (2013.01); *G01N 15/0205* (2013.01); *G01N 2015/0046* (2013.01); *G06N 20/00* (2019.01)

(58) Field of Classification Search
CPC ........... G01N 33/0027; G01N 15/0205; G01N 2015/0046
See application file for complete search history.

(56) References Cited

U.S. PATENT DOCUMENTS 8,009,290 B2 8/2011 Unger
8,907,803 B2 12/2014 Martin
(Continued)

FOREIGN PATENT DOCUMENTS

CN 103245637 A 8/2013
WO 2009021123 A1 2/2009
WO 2015189089 12/2015

OTHER PUBLICATIONS

Arling et al., "Air Quality Sensor Network for Philadelphia—Data Validation—", 2010.*
(Continued)

*Primary Examiner* — Catherine T. Rastovski
(74) *Attorney, Agent, or Firm* — Amin, Turocy & Watson, LLP

(57) ABSTRACT

Techniques for monitoring particulate matter (PM) mass concentration using relatively low cost devices are described. A computer-implemented method comprises determining, by a device operatively coupled to a processor, relationships between: first PM mass data determined by a monitor station device for a first atmospheric area over a period of time; first PM count data determined by a reference PM count device for the first atmospheric area over the period of time; and first conditional information comprising first values for defined conditional parameters, wherein the first values are associated with the first atmospheric area over the period of time. The method further includes generating an initial conversion model based on the relationships, wherein the conversion model converts a PM count to a PM mass based on one or more conditional parameters of the defined conditional parameters and features for updating the conversion model.

19 Claims, 10 Drawing Sheets

Related U.S. Application Data continuation of application No. 15/362,286, filed on Nov. 28, 2016, now Pat. No. 10,393,714.

(51) Int. Cl.
*G01N 15/00* (2006.01)
*G06N 20/00* (2019.01)

(56) References Cited

U.S. PATENT DOCUMENTS

| | | | |
|---|---|---|---|
| 9,995,667 B2 * | 6/2018 | Hart | G01N 21/53 |
| 10,914,716 B2 * | 2/2021 | Wang | G01N 15/0205 |
| 2016/0116390 A1 | 4/2016 | Tan | |
| 2016/0153884 A1 | 6/2016 | Han et al. | |

OTHER PUBLICATIONS

Arling, et al., "Air Quality Sensor Network for Philadelphia," May 6, 2010, 8 pages.
Steinle, et al., "Personal Exposure Monitoring Of PM2.5 in Indoor and Outdoor Microenvironments," Science of the Total Environment 508 (2015), pp. 383-394.
Office Action for U.S. Appl. No. 15/362,286 dated Nov. 1, 2018, 46 pages.
"Met One Instrument,Inc., BAM-1020 Continuous Particulate Monitor" accessed from https://metone.com/Vair-quality-particulate-measurementlregulatory/bam-1020/ on Oct. 28, 2018.
List of IBM Patents or Applications Treated as Related.
Office Action for U.S. Appl. No. 16/437,848 dated Mar. 26, 2020, 48 pages.

* cited by examiner

700

702 — DETERMINING, BY ONE OR MORE COMPONENTS OPERATIVELY COUPLED TO A PROCESSOR, RELATIONSHIPS BETWEEN FIRST PARTICULATE MATTER MASS DATA, FIRST PARTICULATE MATTER COUNT DATA AND FIRST CONDITIONAL INFORMATION,

WHEREIN THE FIRST PARTICULATE MATTER MASS DATA WAS DETERMINED BY A MONITOR STATION FOR A FIRST ATMOSPHERIC AREA OVER A PERIOD OF TIME,

WHEREIN THE FIRST PARTICULATE MATTER COUNT DATA WAS DETERMINED BY A REFERENCE PARTICULATE MATTER COUNT DEVICE FOR THE FIRST ATMOSPHERIC AREA OVER THE PERIOD OF TIME, AND

WHEREIN THE FIRST CONDITIONAL INFORMATION COMPRISES FIRST VALUES FOR DEFINED CONDITIONAL PARAMETERS, WHEREIN THE FIRST VALUES ARE ASSOCIATED WITH THE FIRST ATMOSPHERIC AREA OVER THE PERIOD OF TIME

704 — DETERMINING, BY THE ONE OR MORE COMPONENTS, A CONVERSION MODEL BASED ON THE RELATIONSHIPS, WHEREIN THE CONVERSION MODEL CONVERTS A PARTICULATE MATTER COUNT TO A PARTICULATE MATTER MASS BASED ON ONE OR MORE CONDITIONAL PARAMETERS OF THE DEFINED CONDITIONAL PARAMETERS

FIG. 7

PARTICULATE MATTER MONITORING

FIELD

The present invention relates to particulate matter monitoring and in particular to monitoring particulate matter mass concentrations in real-time using relatively low cost devices.

BACKGROUND

Particulate matter (PM), also known as particle pollution, can be a complex mixture of extremely small particles and liquid droplets in the air. Particles with diameters that are 10 micrometers (μm) and smaller are generally referred to as $PM_{10}$ and those that are 2.5 μm and smaller are generally referred to as $PM_{2.5}$. Both $PK_{10}$ and $PM_{2.5}$ are of particular concern due to their potential for penetrating the deepest parts (including the gas exchange regions) of the lungs and the damaging effects they can have the respiratory and cardiovascular systems.

Organizations such as the World Health Organization (WHO) and various government agencies measure and report PM levels based on PM mass concentration, which is the mass of deposited or captured particles per air sampling volume, measured in micrograms per meter cubed ($\mu g/m^3$). In order to limit individual exposure to $PK_{10}$ and $PM_{2.5}$ mass concentrations, monitoring techniques are becoming of increasing importance worldwide.

However, existing instruments/techniques for measuring PM mass concentrations are subject to shortcomings in efficiency, high costs, and/or accuracy. For example, some PM mass concentration measurement instruments/techniques do not provide mass concentration measurements in real-time (i.e., they can report only hourly and daily averages). These instruments/techniques include those that employ a gravimetric method, a microbalance method (e.g., a tapered element oscillating microbalance (TEOM) device, a quartz crystal microbalance QCM device, and the like), and/or a beta attenuation monitoring (BAM) method to determine PM mass concentration. These instruments/techniques are also very are costly, have deployment restrictions (e.g. additional shelter), and have frequent maintenance/calibration needs. Some optical instruments/techniques (such as those based on the Lorenz-Mie-Debye solution, also referred to herein as a "Mie devices") have been employed to measure PM information at lower costs than instruments that rely on gravimetric measurements, microbalance methods or BAM. However these optical instruments/techniques do not measure PM mass concentration. On the contrary, these optical instruments/techniques are generally only capable of measuring particle count and roughly measuring particle size.

SUMMARY

The following summary is intended to provide a basic understanding of one or more embodiments of the present invention. This summary is not intended to identify key or critical elements, or delineate any scope of the particular embodiments or any scope of the claims. Its sole purpose is to present concepts in a simplified form as a prelude to the more detailed description presented later. One or more embodiments of the present invention described herein include, systems, computer-implemented methods, and/or computer program products.

In one or more embodiments, a computer-implemented method is provided. The computer-implemented method comprises determining, by one or more components operatively coupled to a processor, relationships between first particulate matter mass data, first particulate matter count data and first conditional information, wherein the first particulate matter mass data was determined by a monitor station for a first atmospheric area over a period of time, wherein the first particulate matter count data was determined by a reference particulate matter count device for the first atmospheric area over the period of time, and wherein the first conditional information comprises first values for defined conditional parameters, wherein the first values are associated with the first atmospheric area over the period of time. The method further includes determining, by the one or more components, a conversion model based on the relationships, wherein the conversion model converts a particulate matter count to a particulate matter mass based on one or more conditional parameters of the defined conditional parameters.

Other embodiments include a system and a computer program product that facilitate monitoring particulate matter mass concentrations in real-time using relatively low cost devices.

BRIEF DESCRIPTION OF THE DRAWINGS

FIG. 7 illustrates a flow diagram of an example, non-limiting computer-implemented method that facilitates monitoring PM mass concentration using relatively low cost devices in accordance with one or more embodiments of the present invention.

DETAILED DESCRIPTION

Figure 1:
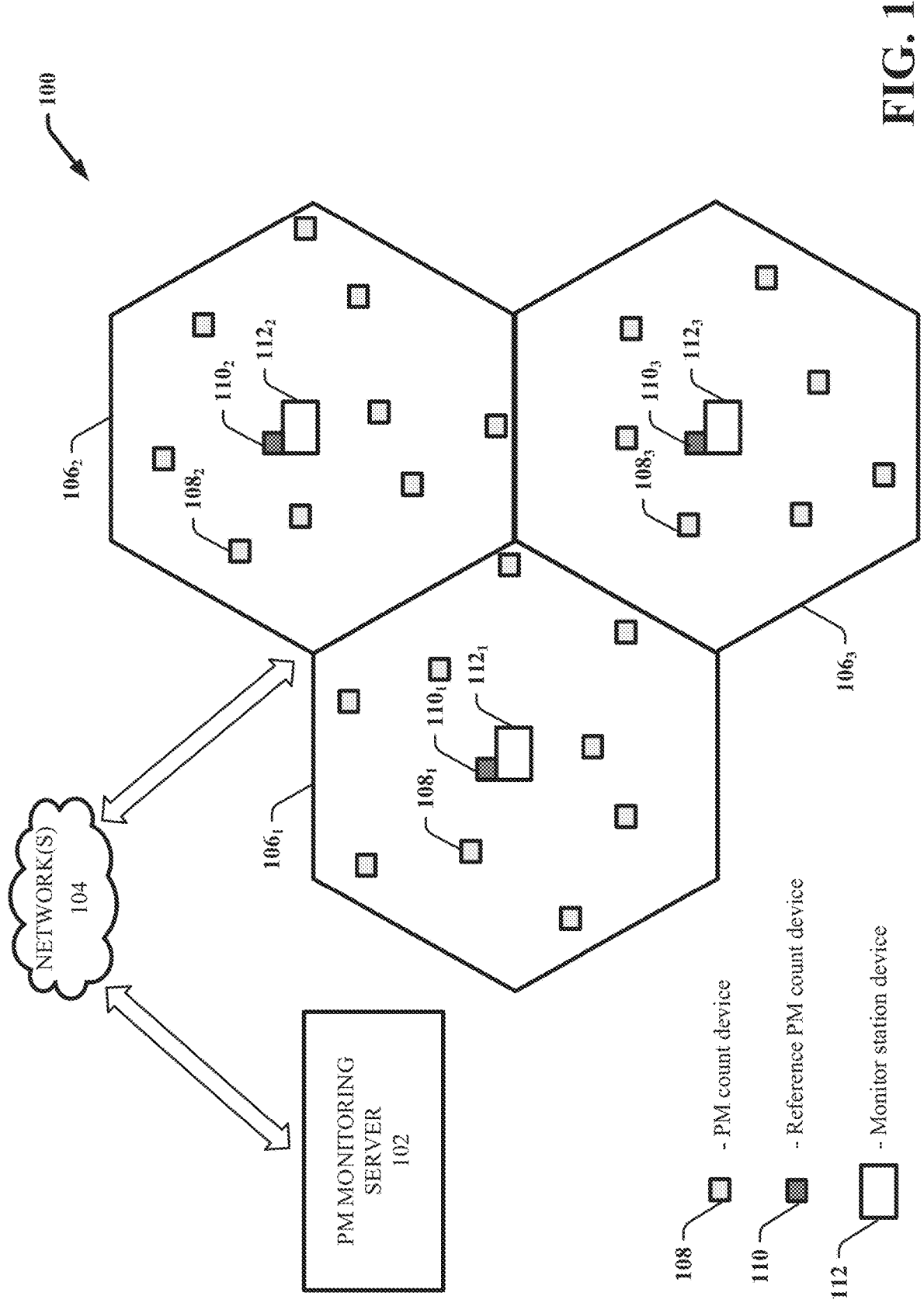
FIG. 1 illustrates an example, non-limiting system that facilitates monitoring PM mass concentration using relatively low cost devices in accordance with one or more embodiments of the present invention.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

The present invention is directed to improved computer processing systems, computer-implemented methods, and/or computer program products that facilitates monitoring particulate matter (PM) mass concentrations.

Some embodiments of the present invention facilitate accurate and real-time measurement of PM mass concentration using relatively low cost devices. In particular, PM count data and/or PM particle size distribution data can be obtained from relatively low cost devices and in real-time. This PM count and/or PM particle size distribution data can then be converted into a PM mass concentration measurement using a conversion model developed based on reference PM mass concentration measurements generated using high cost PM mass concentration instruments (e.g., instruments that employ gravimetric methods, microbalance methods and/or BAM methods to measure PM mass concentration) deployed at one or more regulatory monitoring stations. This reference PM mass concentration data is also referred to herein as "monitor station data." As used herein, the term "real-time" can mean capturing and processing optical sensor based particle count data and/or particle size data to determine a PM mass concentration within a defined number of minutes or seconds (e.g., within 10 seconds, within 30 seconds, within 60 seconds, within 2 minutes) after the optical sensor based particle count data and/or particle size data is captured.

In various embodiments, the conversion model converts PM count and/or size distribution data to mass concentration based on one or more defined conditional parameters. The conversion model can be initially developed based on comparison of reference optical sensor data with monitor station data captured for an atmosphere over an initial sampling period, wherein a reference optical sensor (e.g., a Mie device) can be located at or near a same physical location as the monitor station. The reference optical sensor data can include PM count/size distribution measurements for respective air samples measured over the sampling period. The monitor station data can include mass concentration values associated with the respective air samples determined by a standardized monitor station instrument, (e.g., a TEOM device, a QCM device, a BAM device and the like). Each of the respective samples can also be associated with conditional information including measured values for one or more defined conditional parameters that may have an effect of PM mass concentration. These conditional parameters can include weather related parameters (e.g., temperature, humidity, wind speed, etc.), particle composition distribution, accumulated pulse height (APH), accumulated pulse area (APA) and relative direct current (DC) offset. Using machine learning, correlations between mass concentration values and values for PM count, PM size distribution, and one or more of the conditional parameters are identified and the conversion model can be developed. The conversion model is then applied to convert new PM count/size distribution data determined by an optical sensor device (e.g., a Mie device) that is not located near a monitor station device to mass concentration based on current conditional information associated with the new PM count/size distribution data. In addition, the conversion model can be optimized or updated in real-time based on new data captured by the reference optical sensor and the monitor station.

Aspects of systems, computer program product and/or processes in accordance with the present invention disclosure can be implemented as machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

By way of overview, some embodiments enable real-time determination of PM mass concentration using a conversion model that converts PM count and/or size distribution data to PM mass concentration data based on various defined conditional parameters. Some embodiments of the conversion model of system 100 can be tailored to different geographic locations and pollution levels and fined tuned in real-time using machine learning techniques. In some embodiments, the accuracy of the conversion model can be enhanced using novel parameters including but not limited, accumulated pulse height (APH), accumulated pulse area (APH) and relative direct current (DC) offset.

Some embodiments use relatively low cost optical PM count and/or size distribution measurement instruments and thus improve processing costs otherwise involved with determining PM mass concentrations. Some embodiments facilitate a large scale deployment of optical PM count size distribution measurement instruments across various geographic locations in real-time.

Some embodiments can be implemented through computer hardware and/or software to solve problems that are highly technical in nature and not abstract. For example, some embodiments of system 100 (FIG. 1) can be embodied in computer hardware and/or software to perform operations including receiving and extracting PM data and associated conditional information from a plurality of devices via one or more networks, processing the PM data and conditional information to develop mass concentration conversion models, and employing the mass concentration models to determine PM mass concentrations in real-time based on PM count and size distribution data generated by relatively low cost optical sensing devices. Further, some of the processes involved may be performed by specialized computers for carrying out defined tasks related to real-time PM monitoring.

Referring now specifically to FIG. 1, system 100 can include a plurality of PM count devices 108 respectively dispersed throughout one or more geographical areas 106. It should be appreciated that although three geographical areas $106_{1-3}$ are shown, the number of geographical areas 106 can vary. For example, the subject PM monitoring techniques can be applied to a single geographical area or a plurality of geographical areas. In addition the size, distribution and location of the geographical areas 106 can vary. For example, the respective geographical areas 106 can include different cities located within a same geographical region, different cities respectively located within different geographical regions, different suburbs of a single city, different states, different countries, etc. In various implementations, the geographical areas 106 are respectively associated with different environmental conditions that impact PM mass concentrations in the outdoor atmospheres respectively associated with the geographical areas.

Each of the geographical areas 106 further include monitor station devices 112 that are respectively paired with reference PM count devices 110 located near the respective monitor station devices 112. In particular, the respective reference PM count devices 110 can be located within a defined physical distance from their respective monitor station devices 112 such that the respective pairs of devices are exposed to the same or substantially the same atmospheric conditions. For example, in some implementations the respective reference PM count devices 110 can be located on or within a same physical structure as their respective monitor station devices 112. In another example, the respective reference PM count devices 110 can be located within N meters of their respective monitor station devices 112 (e.g., wherein N can be 100, 75, 50, 25, 10, 5, or 1). It should be appreciated that each geographical area 106 is shown with a single monitor station device 112 and reference PM count device 110 pair, merely for exemplary purposes and that the respective geographical areas 106 can include any number N (wherein N can be one or more) of monitor station device 112 and reference PM count device 110 pairs. Further, the relative locations of the monitor station device 112 and reference PM count device 110 pairs can vary within the respective geographical areas 106.

In one or more embodiments, the monitor station devices 112 can respectively include standardized or certified instruments that accurately and directly measure the mass of deposited or captured particles per air sampling volume, measured in $\mu g/m^3$. For example, in some implementations, the monitor station devices 112 can include instruments that measure PM mass concentration using gravimetric measurement. In another implementation, the monitor station devices 112 can include instruments that measure PM mass concentration using a quartz crystal microbalance, a tapered resonator, an impactor, or weighing filters and sieves. In another implementation, the respective monitor station devices 112 can include one or more TEOM devices and/or QCM devices. In yet another implementation, the respective monitor station devices 112 can include one or more BAM devices. Still in yet another implementation, the respective monitor station devices 112 can include a combination of the aforementioned devices/instruments. In some embodiments, the instruments employed by the respective monitor station devices 112 can vary so long as the respective monitor station devices 112 can accurately and directly measure the mass of deposited or captured particles per air sampling volume. In some implementations, the monitor station devices 112 can also include or be associated with one or more additional sensors or instruments that measure various types of environmental conditions and parameters that can have an impact on PM mass concentrations. For example, such additional sensors can include but are not limited to: temperature sensors, humidity sensors, wind speed and direction sensors, and the like. Further, in some embodiments, the monitor station devices 112 can include one or more instruments that measure additional characteristics associated with PM monitoring, including but not limited to, particle size distribution and particle composition (e.g., a CSIRO® $PM_{2.5}$ high volume sampler device, an ANSTO® $PM_{2.5}$ ASP volume sampler device, and an OSIRIS® fine particle monitor, and other particulate monitoring instruments capable of measuring particulate composition).

In some embodiments (unlike the monitor station devices 112), the PM count devices 108 and reference PM count devices 110 can include relatively low cost optical sensor devices that measure PM count data and/or PM size distribution data (as opposed to PM mass concentration) based on light scattered or attenuated by the particles (e.g., Mie devices). For example, the PM count devices 108 and the reference PM count devices 110 can employ a light source (e.g., a laser diode) to illuminate particles in sampled air. In one example implementation, this light source shines through an optical block including mirrors and one or more photo-detectors. The sampled air can be drawn through the laser beam by a small vacuum pump. As the drawn air particles pass through the laser beam, the laser light interacts with particles and can be scattered. As the light scatters, it can be picked up by the mirrors, which focus the scattered light onto the one or more photo-detectors. The one or more photo-detectors convert the burst of light energy from each particle into a pulse of electrical energy. In various implementations, the PM count devices 108 and the reference PM count devices 110 can determine the number of particles in a sampled volume of air by counting the number of electrical pulses generated. The PM count devices 108 and the reference PM count devices 110 can determine the size of each particle by measuring the height of the electrical signal each particle generates and referencing the height to a calibration curve.

In one or more embodiments, the PM count devices 108 and the reference PM count devices 110 can provide particle count data and/or particle size distribution data in real-time or substantially real-time using the aforementioned light scattering techniques applied to continuously or regularly sampled air. PM count data refers to the number of particles per volume sampled (e.g., in $m^3$) and size distribution data provides the relative numbers of particles of different sizes or size rang groups (e.g., in $\mu m$) included in the volume sampled. For example, a sample volume of $\frac{1}{1000}$ $m^3$ could include a total particle count of about 222,041 and a size distribution wherein 222,041>0.3 um, 20,036>0.5 um, 1,229>1.0 um, 203>2.5 um, 48>5 um, and 22>10 um. PM count data and size distribution data captured by the subject PM count devices 108 and reference PM count devices 110 can vary based on the sensitivity and flow rate of the respective devices and the sampling rate of the respective devices. The sensitivity of an airborne particle counter refers to the size of the smallest particle the unit can detect. In various implementations, the PM count devices 108 and reference PM count devices 110 particle can have sensitivities of at least 0.1 $\mu m$, 0.3 $\mu m$, or 0.5 $\mu m$. The flow rate of a particle counter can be the rate at which its pump draws the sample air through the sample chamber. The higher the flow rate, the more data the counter collects per time period or the faster it can collect a specified volume. In one or more embodiments, the subject PM count devices 108 and reference PM count devices 110 can have flow rates between about 1.0 liters per minute (LPM) and about 100 LPM. The sampling rate of the subject PM count devices 108 and reference PM count devices 110 can also vary. For example, in some implementations, the PM count devices 108 and the reference PM count devices 110 can continuously measure defined volumes of air at a defined flow rate. In other implementations, the PM count devices 108 and the reference PM count devices 110 can measure defined volumes of air at a defined flow rate according to a defined schedule (e.g., once every 10 minutes, once an hour, twice a day, once a day, etc.).

In some embodiments, the PM count devices 108 and reference PM count devices 110 can also includes one or more additional sensors additional sensors or instruments that measure various types of environmental conditions and parameters that can have an impact on PM mass concentration determinations. For example, such additional sensors can include but are not limited to: temperature sensors, humidity sensors, wind speed and direction sensors, and the like. In various embodiments, the PM count devices 108 and the reference PM count devices 110 include the same features and functionalities. For example, the PM count devices 108 and the reference PM count devices 110 can differ only with respect to where the respective devices are located, wherein a reference PM count devices 110 can be located near (e.g., at a same physical location as) a monitor station device 112 and a PM count device 108 can be located away (e.g., outside a defined distance) from a monitor station device 112. In other embodiments, the PM count devices 108 and the reference PM count devices 110 may include some different features and functionalities. For example, the reference PM count devices 110 may be configured to measure PM count data and/or size distribution data at higher sampling rate relative to the PM count devices 108, or vice versa. In another example, the reference PM count devices 110 may be configured with additional environmental sensors (e.g., temperature sensors, humidity sensors, wind sensors, etc.) relative to the PM count devices 108, or vice versa.

In some embodiments, the PM count devices (e.g., the PM count devices 108 and the reference PM count devices 110) can be made substantially smaller, less complex, less costly, and more portable relative to the monitor station devices 112. For example, in some implementations, the PM count devices can be contained within a housing that is about the size of a residential switchboard panel box. In contrast a monitor station device 112 is a relatively high cost instrument that requires regular maintenance and calibration. Many monitoring station devices thus require dedicated structures (e.g., sheds, buildings, etc.) to house them. The structures are often located at protected facilities. Accordingly, the PM count devices (e.g., the PM count devices 108 and the reference PM count devices 110) can be relatively easily deployed in several locations within a defined geographical area as well as many different geographical areas, thereby facilitating a large scale PM monitoring network within the defined geographical area and across the many different geographical areas.

System 100 further includes a PM monitoring server 102 and one or more communication networks 104. In various embodiments, the respective PM count devices 108, reference PM count devices 110, and the monitor station devices 112 can be communicatively connected to the PM monitoring server 102 via the one or more networks 104. Such networks 104 can include wired and wireless networks, including, but not limited to, a cellular network, a wide area network (WAN) (e.g., the Internet) or a local area network (LAN). For example, the respective PM count devices 108 can, the reference PM count devices 110 and the monitor station devices 112 can communicate with the PM monitoring server 102 (and vice versa) using virtually any desired wired or wireless technology, including but not limited to: wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Zigbee and other 802.XX wireless technologies and/or legacy telecommunication technologies, BLUETOOTH®, Session Initiation Protocol (SIP), ZIGBEE®, RF4CE protocol, WirelessHART protocol, 6LoWPAN (IPv6 over Low power Wireless Area Networks), Z-Wave, and/or an ultra-wideband (UWB) standard protocol.

Accordingly, in various embodiments, the devices and components of system 100 establish a large scale sensor network wherein the PM count devices 108, the reference PM count devices 110 and the monitor station devices 112 can respectively provide the PM monitoring server 102 with data respectively measured or collected by the respective devices in real-time (e.g., in response to measurement or collection by the respective devices). In one or more embodiments, based in part on the data received by the respective devices, the PM monitoring server 102 can determine PM mass concentrations associated with the respective geographical areas 106 in real-time (e.g., as the data is received). In particular, the PM monitoring server 102 can employ a conversion model that converts PM count data and/or PM particle size distribution data obtained from the PM count devices 108 respectively included in the geographical areas 106 to PM mass concentration based on various defined conditional parameters that have been determined to have a known effect on PM mass concentration. For example, these conditional parameters can include weather related parameters among various others discussed herein. In some embodiments, the values for the conditional parameters can be measured by the PM count devices 108, the reference PM count devices 110 and/or the monitor station devices 112 and provided to the PM monitoring server 102 by the respective devices in real-time. In other implementations, the PM monitoring server 102 can receive values for the defined conditional parameters from one or more external sources and/or determine the values for the defined conditional parameters internally.

In particular, in addition to particle count and particle size distribution, PM mass concentration can vary based on a variety of factors including but not limited to weather related parameters, such as temperature, humidity, wind speed, wind direction, and other weather or environmental factors. PM mass concentration can also vary based on PM particle composition distribution, meaning the different types of particles included in the sampled air and the respective amounts of the different types of particles. In addition, PM mass concentration can vary based on the geographical characteristics of the landmass associated with a particular atmosphere, such as the natural topography of the land, natural geographical structures, land elevation, atmospheric pressure, the source of the pollutant, the strength of the sun light, temperature, humidity, wind condition, diffusion condition, etc. PM mass concentration can also vary based on various human activities and manmade structures associated with a particular atmosphere.

In one or more embodiments, the PM monitoring server 102 can initially generate the conversion model based on reference PM measurement data generated by each reference PM count device 110 and monitor station device 112 pair over a defined sampling period, and based on conditional information including measured values, respectively associated with the geographical areas 106 of each reference PM count device 110/monitor station device 112 pair, for various defined conditional parameters over the defined sampling period. For example, with respect to a single geographical area 106₁, the PM monitoring server 102 can receive PM mass concentration data measured by the monitor station device $112_1$ included in the geographical area $106_1$ over a defined sampling period of time. For example, the sampling period of time can include a day, a week a month, a year etc. It should be appreciated that this period of time can vary. The PM mass concentration data will thus include measured PM mass concentration values for respective air samples from the atmosphere associated with the geographical area $106_1$ over the defined period of time. The sampling rate over the defined period of time can also vary based on the type of PM mass concentration measurement equipment employed by the monitor station devices $112_1$. For example, the PM mass concentration measurements can be determined every 10 minutes, once an hour, twice a day, once a day, etc.

The PM monitoring server 102 can further receive PM count data and/or PM size distribution data measured by the reference PM count device $110_1$ associated with the monitor station device $112_1$ over the sampling period. The PM count data and/or PM size distribution data will thus include measured PM counts and/or size distributions for respective air samples from the atmosphere associated with the geographical area $106_1$ over the sampling period. The PM monitoring server 102 can further correlate the PM mass concentration values with the PM counts and/or size distributions for air samples measured by the respective devices at or near the same time. For example, in some embodiments, the monitor station device $112_1$ and the reference PM count device $110_1$ can be calibrated to measure air samples at the same time and at the same sampling rate. In other embodiments, the sampling rates of the monitor station device 112 and the reference PM device $110_1$ can vary and the PM monitoring server 102 can employ average measurements from one or both devices associated with a same time point (e.g., average measurements for the hour, the day, etc.).

In addition to PM mass concentration values generated by the monitor station device $112_1$ and corresponding count/size distribution measurements generated by the reference PM count device $110_1$ over the defined sampling period, the PM monitoring server 102 can further receive and/or determine values for defined conditional parameters associated with the geographical area $106_1$ and each of the mass concentration values and PM count/size distribution measurements over the period of time. For example, the PM monitoring server 102 can associate a temperature measurement, a humidity measurement, a wind measurement, particle composition distribution information, and values for other defined conditional parameters, with each received mass concentration value and corresponding PM particle count/size distribution measurement over the sampling period.

Based on all the data received for the geographical area $106_1$ over the initial sampling period (e.g., PM mass concentration values, corresponding PM counts/size distributions, and corresponding conditional parameter values), using machine learning, the PM monitoring server 102 can identify patterns in the data and generate a conversion model that converts a PM count and/or size distribution to a mass concentration value based on one or more of the defined conditional parameters. For example, in one implementation, the conversion model can include a linear regression model that determines PM mass concentration as a function of particle count, particle size distribution, particle composition distribution, temperature, humidity, wind speed, wind direction, etc.

The PM monitoring server 102 can receive or determine the same or similar data (e.g., mass concentration values, count/size distribution measurements, and conditional parameter values) for each of the respective geographical areas 106 from their respective monitor station device 112 and reference PM count device 110 pairs (over the same sampling period of a different sampling period). In some embodiments, the PM monitoring server 102 can pool all data received for each different geographical areas 106 to develop a single model that is applicable to all the respective areas. In other embodiments, the PM monitoring server 102 can generate different conversion models for the respective geographical area 106 based on the data respectively associated with each of the different geographical areas. In particular, a variety of constant and/or variable environmental and/or human based conditions associated with the respective geographical areas 106 may have different effects on PM mass concentration and/or how certain conditional parameters of the defined conditional parameters effect PM mass concentration. For example, a conversion model for an urban area could be much different from that of suburban area because the composition of the pollutant may be very different. Accordingly, in some embodiments, the PM monitoring server 102 can develop custom conversion models for the different geographical areas that account for variables that are unique to the respective geographical areas. For example, the respective models may vary based on the types of conditional parameters evaluated and/or weights applied to common conditional parameters.

After the PM monitoring server 102 has developed an initial conversion model (or models), the PM monitoring server 102 can employ the conversion model (or models) to convert current PM count/size distribution data received from the PM count devices 108 to PM mass concentration values based on current values for the relevant conditional parameters measured or determined at or near the same time as the current PM count/size distribution data was generated. In addition, the PM monitoring server 102 can regularly or continuously (e.g., in real-time) update or optimize the conversion model (or models) using machine learning over time based on new PM data generated by the respective reference PM count devices 110 and their paired monitor station devices 112 over time, new conditional information respectively associated with the new PM data, and patterns in historical data received over time.

In various embodiments, in order to improve the accuracy of the conversion model (or models), the PM monitoring server 102 can employ some additional conditional parameters associated with optical sensor device measurements to better characterize the PM count data and/or particle size distribution data. These additional conditional parameters are referred to herein as accumulated pulse height (APH), accumulated pulse area (APA), and relative direct current (DC) offset. In particular, as discussed above the subject PM count devices 108 and reference PM count devices 110 can include optical sensors that measure electrical pulses generated based on light scattered by PM particles in sampled air. The PM count devices 108 and the reference PM count devices 110 can determine the number of particles based on the number of electrical pulses, wherein the number of pulses generally directly corresponds to the number of particles. The PM count devices 108 and the reference PM count devices 110 can also determine the heights of the respective particles based on the respective heights of the pulse signals, wherein the particle size linearly increase with pulse height. However, due to the irregular shapes of many particles, the pulse height may inaccurately reflect particle size. For example, the particular two-dimensional surface of a particle that receives and reflects measured light may be smaller or larger relative to the total volume of the particle, causing the particle's resulting pulse height to indicate the particle is smaller or larger than it actually is. In order to account for this discrepancy, the PM monitoring server 102 can determine and/or receive information including the APH for an air sample that reflects the total pulse height of particles measured in the sample, and the APA for the sample that reflects the total pulse area of the sample. The PM monitoring server 102 can further factor these parameters into the conversion model to facilitate determining mass concentration.

Figure 2A:
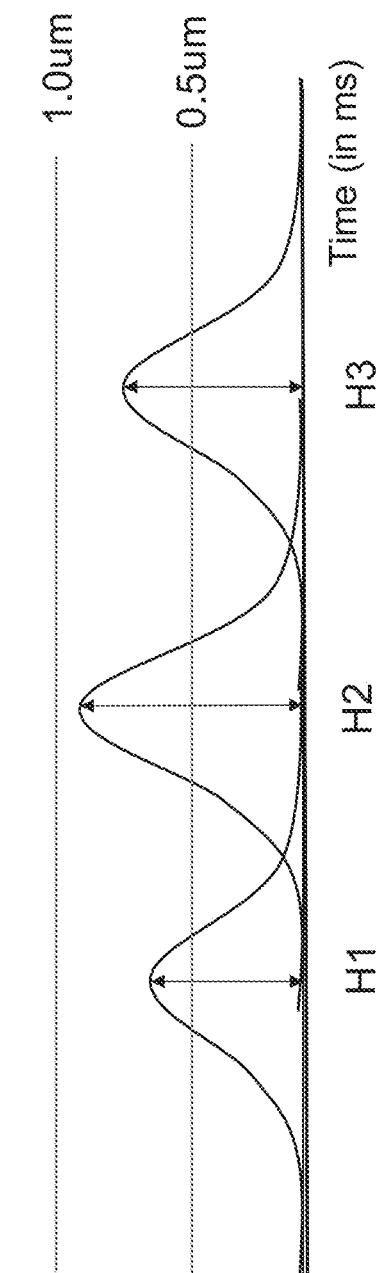
FIG. 2A illustrates a graph depicting measurement of accumulated pulse height (APH) in accordance with one or more embodiments of the present invention.
Figure 2B:
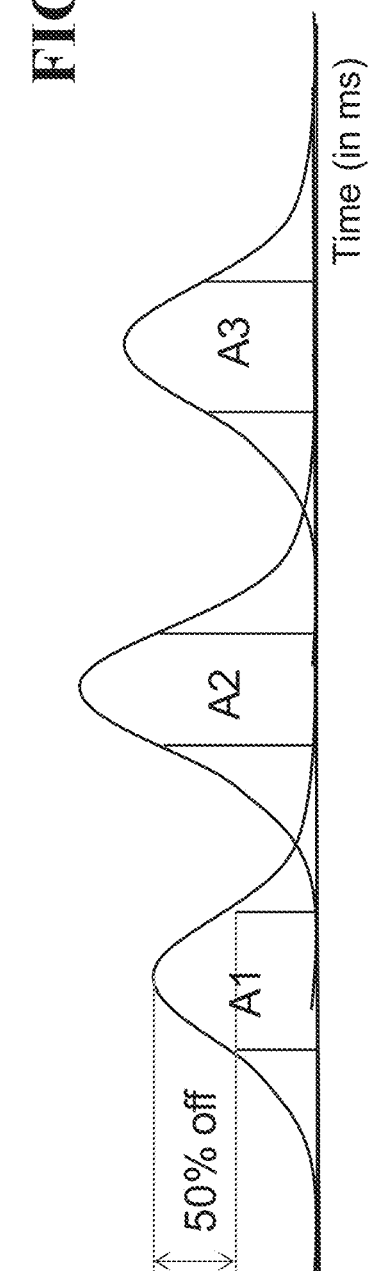
FIG. 2B illustrates a graph depicting measurement of accumulated pulse accumulated pulse area (APA) in accordance with one or more embodiments of the present invention.

FIG. 2A illustrates a graph (201) depicting measurement of accumulated pulse height (APH) in accordance with one or more embodiments of the present invention. FIG. 2B illustrates a graph (202) depicting measurement of accumulated pulse accumulated pulse area (APA) in accordance with one or more embodiments of the present invention. As depicted, graphs 201 and 202 respectively depict three pulse signals generated based on light reflected by particles included in an air sample measured by an optical sensor instrument employed by the subject PM count devices 108 and reference PM count devices 110.

With reference to FIG. 2A, the heights (H1, H2 and H3) of the respective pulses, measured from the curve peak to the baseline, respectively correspond to "pulse height." APH includes the additive total height of the respective pulse heights (H1+H2+H3 . . . ) in a measured sample. With reference to FIG. 2B, the areas (A1, A2, and A3) under the respective curves for each pulse signal respectively correspond to the "pulse area." In some embodiments, the top 50% of the respective curves can be eliminated from the measure pulse area for each pulse signal. For example, for a single pulse wave, the pulse area could be expressed by f(x), wherein f(x) has the highest value at the peak of the pulse wave in position x0. With respect to the value of f(x0), there are two positions that have the value of 0.5*f(x0). One is located on the pulse wave to the left of x0 and the other is located on the pulse wave to the right of x0, referred to x0− and x0+ respectively, where f(x0−)=f(x0+)=0.5*f(x0). The APA includes the additive total area of the respective pulse areas (e.g., A1+A2+A3 . . . ) in a measured sample. Accordingly, the can be calculated using the following formula.

$$APA = \int_{x0-}^{x0+} f(x)dx$$

In some embodiments, the APH and the APA values can be determined by the PM monitoring server 102 based on raw optical sensor data provided to the PM monitoring server 102 by the PM count devices 108 and reference PM count devices 110. In other embodiments, the PM count devices 108 and the reference PM count devices 110 can be configured to determine the APH and the APH values in association with determining PM count measurements and particle size distribution measurements. The PM monitoring server 102 can further factor these parameters into the conversion model, wherein in addition to particle count and/or particle size distribution and one or more of the various other conditional parameters discussed herein (e.g., weather related parameters, particle composition, etc.), mass concentration can be based on a sample's APH and APA.

In addition to particle shape causing inaccurate pulse height readings, in conditions with heavy pollution wherein the atmosphere includes relatively high amounts of particles, optical sensing devices can have difficulty distinguishing clusters of small particles (e.g., $PM_{2.5}$ particles) from single large particles (e.g., $PM_{10}$ particles). Accordingly, in heavy pollution conditions (e.g., characterized by atmospheres with high PM mass concentrations), an optical sensing device, such as those employed by the subject PM count devices 108 and reference PM count devices, may report a smaller amount of small particles and a larger amount of large particles, when in fact the reported large particles are actually condensed clusters of small particles. As a result, in heavy pollution conditions, the optically measured PM count and size distribution data may not accurately reflect the actual PM count and particle size distribution. Thus the mass concentration determined based on the inaccurate PM count and size distribution data may be off from the actual mass concentration.

In order to account for this discrepancy, in one more embodiments, the PM monitoring server 102 can develop different conversion models that are designed to account for different types of pollution conditions/levels. For example, the PM monitoring server 102 can employ various machine learning techniques to identify patterns with respect to how different conditional parameters and conditional parameter values relate to varying mass concentration levels to develop the different conversion models for different levels of pollution. These different conversion models can vary based on the types of conditional parameters evaluated and/or based on weights applied to the respective variables. For example, the PM monitoring server 102 can generate and employ a first conversion model for PM sample data indicative of low pollution levels and further generate and employ a second conversion model for PM sample data indicative of high pollution levels. The first conversion model can include different conditional parameters relative to the second conversion model and/or different weights applied to same conditional parameters included in the second conversion model. For example, the first conversion model may determine mass concentration as a function of particle size, particle size distribution, particle composition distribution, temperature, weather, humidity, and wind speed, and the second conversions model may determine mass concentration as a function of particle size, particle size distribution, particle composition distribution, temperature, weather, humidity, and wind speed, APH and APA. In another example, the first conversion model may determine mass concentration as a function of particle size, particle size distribution, particle composition distribution, temperature, weather, humidity, wind speed, APH and APA, and the second conversions model may determine mass concentration as a function of the same variables yet weight APH and APA more heavily.

In some embodiments, in association with accounting for the discrepancy associated with potential inaccurate pulse height readings in conditions with heavy pollution, the PM monitoring server 102 determine or receive the relative DC offset associated with the electrical pulse signals for a measured PM air sample. The relative DC offset refers to the mean value of the waveform or the offsetting of a signal from zero.

Figure 3:
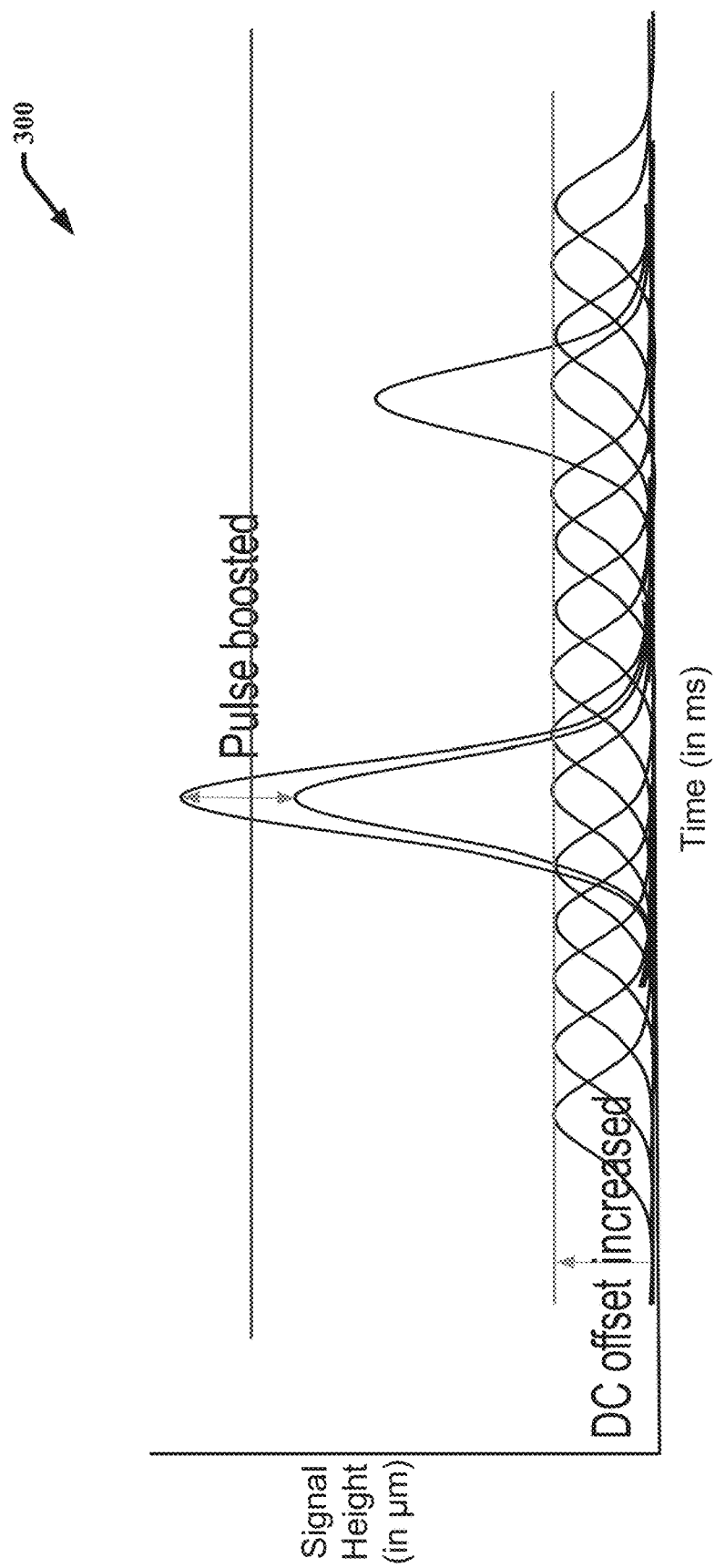
FIG. 3 illustrates a graph depicting the relative DC offset associated with pulse signals for a PM sample in accordance with one or more embodiments of the present invention.

For example, FIG. 3 illustrates a graph 300 depicting the relative DC offset associated with pulse signals for a PM sample in accordance with one or more embodiments of the present invention. Graph 301 includes a plurality of pulse signals generated based on light reflected by particles included in an air sample measured by an optical sensor instrument employed by the subject PM count devices 108 and reference PM count devices 110. A few of the pulse signals have substantially higher amplitudes (or heights) relative to the other signals. This may be a result of the pulses of some large particles in the sample being boosted and pulses of some small particles being undetected. As a result the relative DC offset of the sample can be increased. In some embodiments, the DC offset value for a PM sample can be determined by the PM monitoring server 102 based on raw optical sensor data provided to the PM monitoring server 102 by the PM count devices 108 and reference PM count devices 110. In other embodiments, the PM count devices 108 and the reference PM count devices 110 can be configured to determine DC offset values in association with determining PM count measurements and particle size distribution measurements.

In one implementation, the PM monitoring server 102 can employ the relative DC offset values for air samples to determine the level of pollution associated with respective air samples. For example, the PM monitoring server 102 can determine a first range of DC offset values associated with low pollution states, a second range of DC offset values associated with medium pollution states, and a third range of DC offset values associated with high pollution states. In another example, the PM monitoring server 102 can determine a threshold DC offset value, wherein DC offset values below the threshold value are considered associated with a low pollution state and DC offset values above the threshold DC offset value are considered associated with a high pollution state. Accordingly, in various embodiments, the PM monitoring server 102 can determine whether a measured air sample can be associated with a high pollution state or a low pollution state based on the relative DC offset value for the sample. In embodiments in which the PM monitoring server 102 has different conversion models for different pollution levels, the PM monitoring server 102 can then select the appropriate conversion model to employ to convert the PM count/size distribution data for the sample to mass concentration.

For example, in some embodiments, in order to determine the threshold DC offset value, the PM monitoring server 102 can employ the relative DC offset values for measured PM samples from the reference PM count devices 110 to identify correspondences between the respective DC offset values and mass concentration levels (determined by monitor station devices 112 respectively paired with the PM count devices 110), respectively associated with high pollution levels and low pollution levels. For instance, the PM monitoring server 102 can employ a threshold scheme wherein a previously determined threshold mass concentration level separates high pollution and low pollution states. According to this embodiment, the PM monitoring server 102 can examine seed data including PM count/size distribution measurements determined by a reference PM count device 110, wherein each PM count/size distribution measurement is also associated with a DC offset value and a mass concentration level determined by the monitor station device 112 for the reference PM count device. The PM monitoring server 102 can further identify a subset of the DC offset values associated with the threshold mass concentration level. For example, the PM monitoring server 102 can identify a subset of the DC offset values respectively associated with mass concentration levels within a defined deviation range of the threshold mass concentration level. According to this example, the PM monitoring server 102 can further determine an average DC offset value based on the DC offset values included in the subset and set this average DC offset value as the threshold DC offset value dividing samples associated with low and high pollution states.

In other implementations, the PM monitoring server 102 can apply the relative DC offset value for a sample as a conditional parameter that is part of a conversion model, wherein the model outputs a mass concentration level based on in part on the DC offset value associated with the PM sample data. For example, in one embodiments, the PM monitoring server 102 can be configured to add, subtract, multiply, divide, etc., the initial conversion model mass concentration output by an amount, wherein the amount can be determined based on the particular DC offset value.

Figure 4:
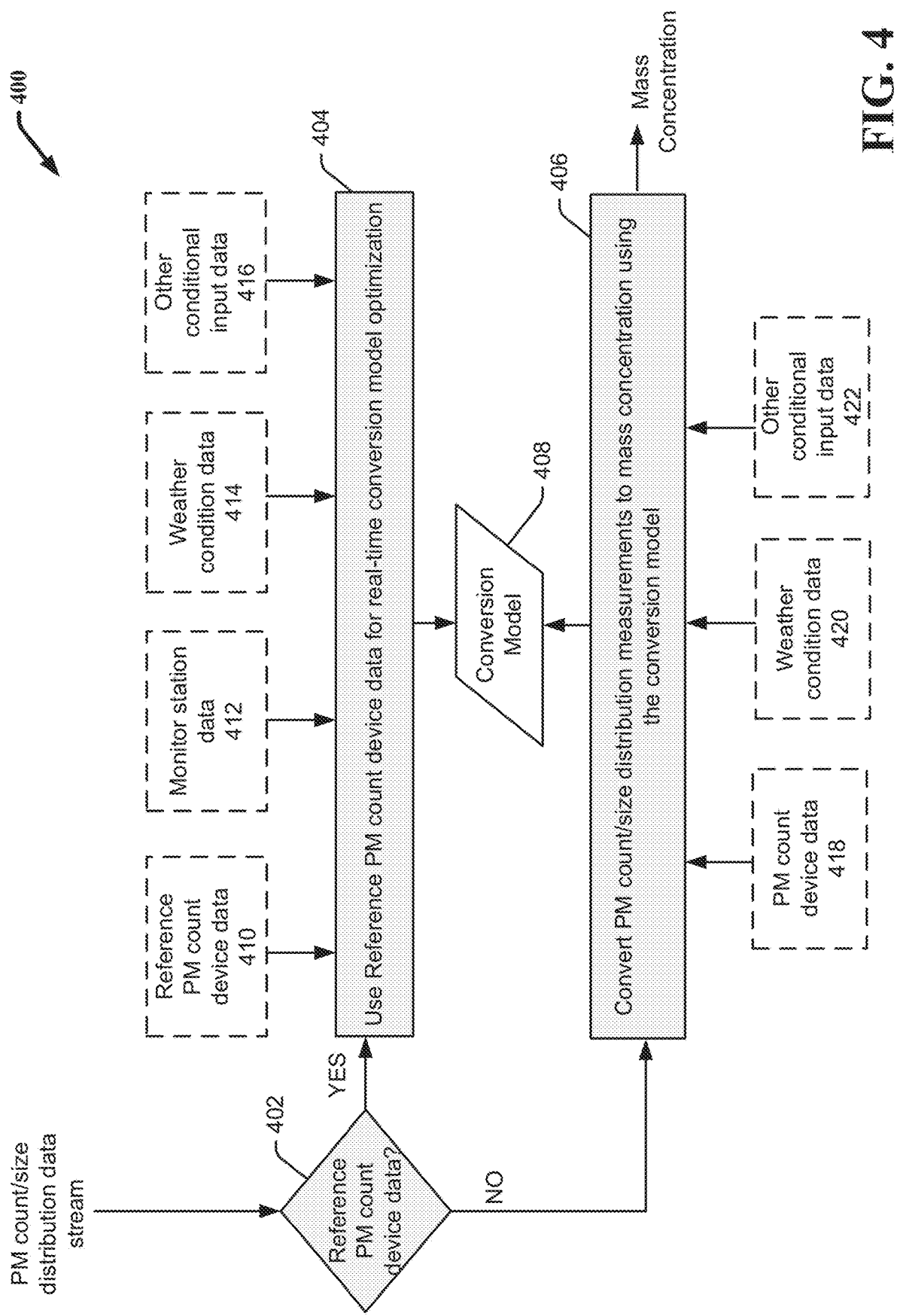
FIG. 4 illustrates a flow diagram of an example, non-limiting process that facilitates monitoring PM mass concentration in real-time using relatively low cost devices in accordance with one or more embodiments of the present invention.

FIG. 4 illustrates a flow diagram of an example, non-limiting process 400 that facilitates monitoring PM mass concentration in real-time using relatively low cost devices in accordance with one or more embodiments of the present invention. In various embodiments, process 400 can be performed by the PM monitoring server 102 of system 100. Repetitive description of like elements employed in respective embodiments is omitted for sake of brevity.

Process 400 demonstrates an example application of system 100 after the PM monitoring server 102 has developed one or more initial conversion models that convert PM count/size distribution data, received for one or more geographic areas, to mass concentration. Process 400 can be employed in association with a single conversion model that applies to PM data received for a single geographic area, a single conversion model that applied to PM data received for several geographic areas, as well as multiple conversion models respectively tailored to PM data associated with different geographic areas.

With reference also now to FIG. 1, the PM monitoring server 102 can receive a periodic or continuous data stream, including PM count and/or particle size distribution data from PM count devices 108 and reference PM count devices 110. For example, the PM count and/or size distribution data stream can include a continuous stream of measurements respectively made by the PM count devices 108 and the reference PM count devices 110 in one or more geographical areas 106. In some embodiments, each PM count and/or particle size measurement can be associated with time information (e.g., a time stamp) that indicates the time when it was measured by the PM count device 108 or reference PM count device 110. For example, the time stamp can be applied by the PM count device 108 or the reference PM count device 110 prior to sending the PM count and/or particle size distribution measurement to the PM monitoring server 102. In another example, in embodiments in which the PM count devices 108 and the reference PM count devices 110 are configured to send measured PM count and/or particle size distribution data to the PM monitoring server 102 in real-time (e.g., in response to measurement of the data), the PM monitoring server 102 can associate time information with the data indicating the time it was received by the PM monitoring server 102. In various embodiment, each PM count and/or size distribution measurement received by the PM monitoring server 102 can also be associated with identification information identifying the device (e.g., a unique device identifier, serial number, etc.) or type of device (e.g., PM count device 108 or reference PM count device 110) that provided the measurement, and/or location information indicating the location of the device. In some embodiments, the PM monitoring server 102 can determine the location of the device based on information accessible to the PM monitoring server 102 associating respective device identifies with locations of the respective devices.

Referring now FIGS. 1 and 4, at 402, for each PM count and/or size distribution measurement received by the PM monitoring server 102, the PM monitoring server 102 determines whether data was provided by a reference PM count device 110 or a PM count device 108. If at 402 the PM monitoring server 102 determines that the PM count and/or size distribution measurement data was provided by a reference PM count device 110, at 404, the reference PM count device data 410 is used to optimize the conversion model 408 in real-time. In particular, the reference PM count device data 410 is provided as an input to optimize the conversion model 408 in real-time, along with monitor station data 412 associated with the reference PM count device data 410 (e.g., PM mass concentration data generated by the monitor station device 112 paired with the reference PM count device 110 at or near the same time as the reference PM count device data 404 was generated), weather condition data 414 associated with the reference PM count device data 410 (e.g., values for defined weather related conditional parameters at or near the time when and location where the reference PM count device data 410 was generated), and other conditional input 416 associated with the reference PM count device data 410 (e.g., particle composition data for the reference PM count device data 404, APH, APA, DC offset, etc.), to optimize the conversion model 408 in real-time. If however, it is determined at 402 that the PM count and/or size distribution measurement data was provided by a PM count device 108, at 406, the PM count device data is converted to a mass concentration using the conversion model 408. In particular, the PM count device data 418 is provided as an input, along with weather condition data 420 associated with the PM count device data 418 (e.g., values for defined weather related conditional parameters at or near the time when and location where the PM count device data 418 was generated), and other conditional input data 422 associated with the PM count device data 418 (e.g., particle composition data for the PM count device data 418, APH, APA, DC offset, etc.) to the conversion model to convert the PM count device data 418 (e.g., PM count/size distribution measurements) into a mass concentration value.

As discussed above, the PM monitoring server 102 can continuously or periodically receive reference PM count device data 410 from reference PM count devices 110 and PM count device data 418 from PM count devices 108 at or near the same time. As a result, the PM monitoring server 102 can regularly or continuously optimize the conversion model 408 in real-time as the PM monitoring server 102 is employing the conversion model to generate mass concentration outputs based on PM count device data 418. Thus in one or more embodiments, at 406 the PM monitoring server 102 will regularly employ the conversion model 408 as optimized in real-time based on reference PM count device data 410 received at or near the same time as PM count device data 418.

Figure 5:
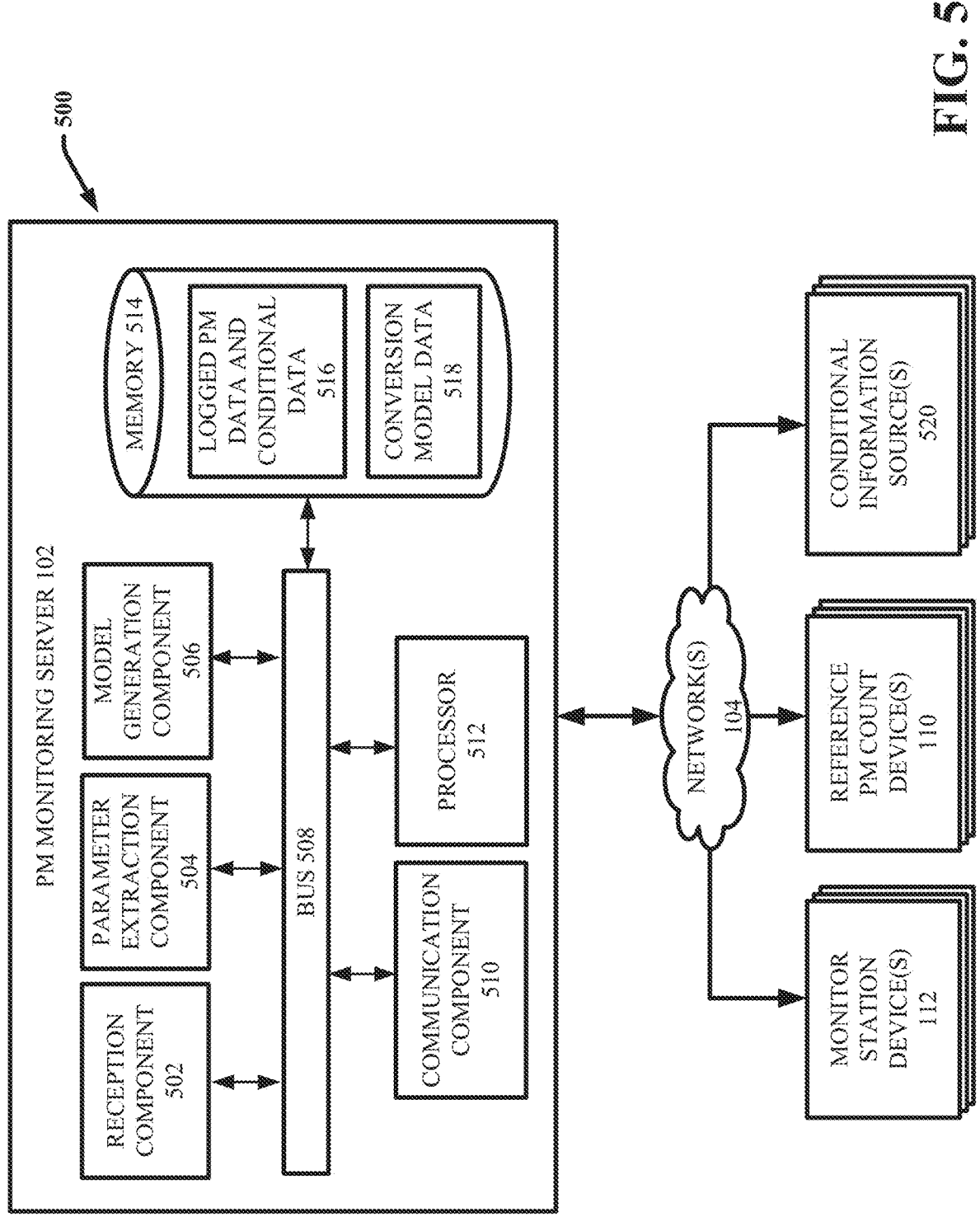
FIG. 5 illustrates a block diagram of an example, non-limiting system that facilitates generating a conversion model that facilitates determining PM mass concentration using relatively low cost devices in accordance with one or more embodiments of the present invention.

FIG. 5 illustrates a block diagram of another example, non-limiting system 500 that facilitates generating a conversion model for determining PM mass concentration using relatively low cost devices in accordance with one or more embodiments of the present invention. System 500 can include same or similar features as system 100. Repetitive description of like elements employed in respective embodiments is omitted for sake of brevity.

As depicted, system 500 (like system 100) includes a PM monitoring server 102, and (communicatively connected via one or more networks 104) one or more monitor station devices 112, and one or more reference PM count devices 110. In some embodiments, each of reference PM count devices 110 is paired with at least one monitor station device 112 and is located within a defined distance to its paired monitor station device 112, such that the respective devices are exposed to the same atmospheric conditions. In various embodiments, each paired reference PM count device 110/ monitor station device 112 is associated with a defined geographical area (e.g., a geographical area 106) and associated atmosphere. System 500 can also include one or more conditional information sources 520, communicatively connected to the PM monitoring server 102 via the one or more networks 104, from which the PM monitoring server 102 can extract and/or receive various types of conditional information associated with one or more atmospheres monitored by the PM monitoring server 102. For example, in some implementations, the one or more conditional information sources 520 can include/provide associated weather condition data 414 to the PM monitoring server 102 information regarding with monitored atmospheres. In another example, the one or more conditional information sources 520 can provide environmental characteristic information associated with a monitored geographical area, such as: topography information, physical characteristics (natural and man-made) of the land, associated human activities, and any other information that may be relevant to the atmosphere in the geographical area of interest, e.g., data from one or more PM Count devices (not depicted). The PM monitoring server 102 can include various computer-executable components, including, but not limited to, reception component 502, parameter extraction component 504, model generation component 506 and communication component 510. The PM monitoring server 102 can also include or otherwise be associated with at least one memory 514 that stores computer-executable components (e.g., the reception component 502, the parameter extraction component 504, the model generation component 506 and the communication component 510). The PM monitoring server 102 can also include or otherwise be associated with at least one processor 512 that execute the computer-executable components stored in the memory 514. The PM monitoring server 102 can further include a bus 508 that can operably couple the various system components including, but not limited to, the reception component 502, the parameter extraction component 504, the model generation component 506, the communication component 510, the memory 514 and/or the processor 512.

Although various components (e.g., the reception component 502, the parameter extraction component 504, the model generation component 506 and the communication component 510) are depicted as part of PM monitoring server 102), in other embodiments, any number of different types of devices can be associated with or include the aforementioned components. All such embodiments are envisaged. For example, one or more of the system components, depicted as co-located with PM monitoring server 102, can be co-located or associated with another device. By way of example (and without limitation), such other devices can include another server (not depicted), an intermediary device (not depicted) between the server and the monitor station device 112, reference PM count devices 110 and conditional information sources 520, one or more of the monitor station device 112, one or more of the reference PM count devices 110, one or more of PM count devices (not shown in FIG. 5), and/or other devices.

The PM monitoring server 102 can include communication component 510 to facilitate wired and/or wireless communication between the PM monitoring server 102 the one or more monitor station devices 112, the one or more reference PM count devices 110, one or more PM count devices (not depicted in FIG. 5)), and the one or more conditional information sources 520. For example, the communication component 510 can be or include hardware (e.g., a central processing unit (CPU), a transceiver, a decoder), software (e.g., a set of threads, a set of processes, software in execution) or a combination of hardware and software that facilitates communicating information between the PM monitoring server 102 and one or more other devices (not depicted).

In various embodiments, the reception component 502 can receive and/or extract information from the one or more monitor station device 112, the one or more reference PM count devices 110 and the one or more conditional information sources 520. In particular, in association with developing one or more conversion models, during an initial sampling period (e.g., a day, a week, a month, etc.), the reception component 502 can receive PM mass concentration measurements for respective air samples measured by the respective monitor station devices 112 at respective times over the course of the sampling period. The reception component 502 can further receive PM count and/or particle size distribution measurements determined by the reference PM count devices 110 for respective air samples measured at or near the respective times over the course of the sampling period. In some embodiments, for each air sample measured by the reference PM count devices 110, the reception component 502 can also receive an APH measurement, an APA measurement and a relative DC offset measurement. In other embodiments, the reception component 502 can receive raw optical measurements from the reference PM count devices 110, the raw optical measurements including waveform information associated with pulse signals generated by the reference PM count devices 110. According to these embodiments, the parameter extraction component 504 can determine information including particle count, particle size distribution, APH, APA and relative DC offset, based on the raw data.

In addition to reference PM data, including particle count/size distribution measured by the reference PM count devices 110, and PM mass concentration data measured by one or more associated monitor station devices 112, the reception component 502 can receive and/or the parameter extraction component 504 determine other conditional information associated with air samples measured during a sampling period. This conditional information can include values for various defined conditional parameters that may have an effect on PM mass concentration, including but not limited to: temperature, humidity, wind speed, wind direction, and particle composition distribution. In some implementations, the monitor station devices 112 and/or the reference PM count devices 110 can measure and provide the PM monitoring server 102 values for at least some of these conditional parameters (e.g., using temperature sensors, humidity sensors, wind speed sensors, particle composition analysis instruments, etc.). In other implementations, the parameter extraction component 504 can identify and extract values for some of the conditional parameters based on conditional information accessible to the parameter extraction component 504 at the one or more conditional information sources 520, the monitor station devices 112 and/or the reference PM count devices 110. In various embodiments, the reception component 502 can receive PM data and associated conditional information from the monitor station devices 112, the reference PM count devices 110 and/or the one or more conditional in real-time over the course of the sampling period. The PM monitoring server 102 can also store all received or determined PM data and conditional data in memory 514 (e.g., as logged PM data and conditional data 516).

In some embodiments, the parameter extraction component 504 can further organize and index received and/or determined PM data and conditional information to facilitate processing by the model generation component 506. For example, the parameter extraction component 504 can associate each mass concentration value determined by a monitor station device 112 with a corresponding PM count measurement (or measurements) and/or PM size distribution measurement (or measurements) measured by the reference PM count device 110 associated with the monitor station device at or near the same time as the mass concentration value was determined. The parameter extraction component 504 can also include information with the PM mass concentration and PM count/size distribution data identifying the measurement time and location associated with the data. The parameter extraction component 504 can further associate each mass concentration measurement and corresponding PM count and/or size distribution data with values for various defined conditional parameters that were measured and/or determined at or near the same time the mass concentration value was determined (e.g., values for weather related conditional parameters, as well as PM particle composition, APH, APH, and relative DC offset). In some embodiments, the logged PM data and conditional data 516 can include the aforementioned information as provided, organized and indexed by the parameter extraction component 504.

In various embodiments, the model generation component 506 can analyze the PM data measured by the reference PM count devices 110, the associated values for various conditional parameters, and the corresponding mass concentration values provided by the monitor station devices 112 respectively paired with the reference PM count devices 110 to determine patterns and correlations between the mass concentration values, the values for PM count, PM size distribution, and the values for the various conditional parameters of the present invention. Using machine learning based on the identified patterns and correlations, the model generation component 506 can generate one or more conversion models that convert a PM count and/or size distribution value to a mass concentration value based on one or more of the conditional parameters. In some embodiments, as described supra, the model generation component 506 can generate different conversion models that air tailored to different geographical areas and/or different pollution levels (e.g., high pollution levels and low pollution levels). The PM monitoring server 102 can further store the conversions models generated by the model generation component 506 in memory 514 (e.g., as conversion model data 518). In implementations in which the model generation component 506 develops different conversion models for different geographical areas and/or different pollution levels, the conversion model data 518 can include information with the respective conversion models identifying the geographical location and/or the pollution level associated with each conversion model.

For example, the model generation component 506 can make inferences based on the patterns and correspondences in the data to develop the one or more conversion models. Such inferences can be probabilistic (e.g., the computation of a probability distribution over states of interest can be based on a consideration of data and events) and involve techniques for composing higher-level events from a set of events and/or data. In various embodiments, the model generation component 506 can make inferences based on the patterns and/or correspondence in the data can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x4, x4, . . . xn), with a certain confidence that the input belongs to a class, such as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is one example (without limitation) of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence. Such classification can also include the use of statistical regression(s) to develop models of priority.

Figure 6:
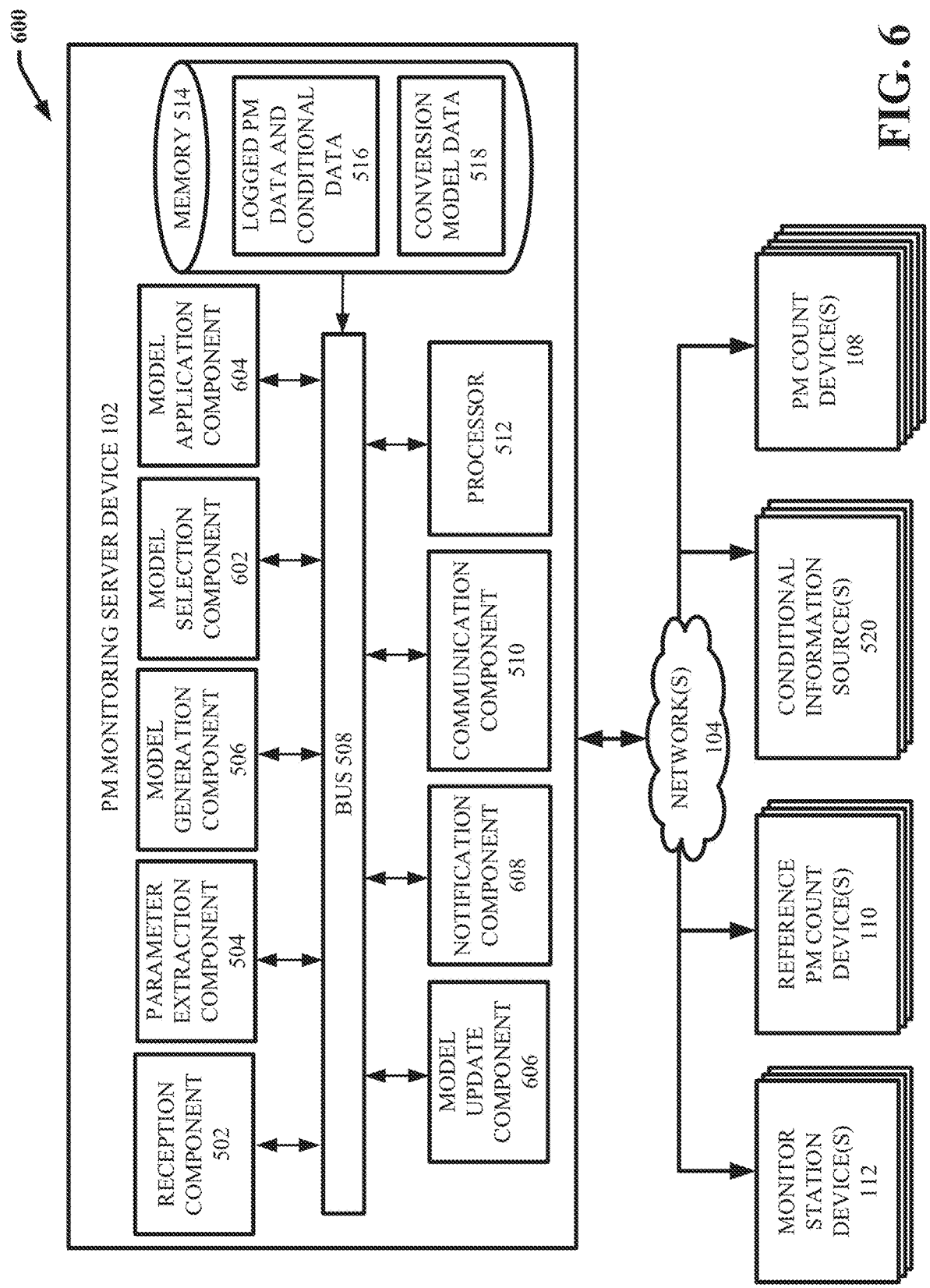
FIG. 6 illustrates a block diagram of an example, non-limiting system that facilitates monitoring PM mass concentration using relatively low cost devices in accordance with one or more embodiments of the present invention.

FIG. 6 illustrates a block diagram of another example, non-limiting system that facilitates monitoring PM mass concentration using relatively low cost devices in accordance with one or more embodiments of the present invention. As depicted, system 600 includes same or similar features as system 500, with the addition of one or more PM count devices 108 and additional computer-executable components to the PM monitoring server 102, including model selection component 602, model application component, model update component 606 and notification component 608. Repetitive description of like elements employed in respective embodiment is omitted for sake of brevity.

As described above, once the PM monitoring server 102 has developed one or more initial conversion models, the PM monitoring server 102 (or another device, such as the PM count devices 108), can use the model application component 604, to determine mass concentration values using the one or more conversion models. In particular, using the one or more conversion modes, the model application component 604 can determine PM mass concentrations, in real-time, based on new PM count data and/or size distribution data provided by PM count devices 108 (e.g., that is not associated with a monitor station device 112) and new values for the one or more defined conditional parameters associated with the new PM count data and/or size distribution data (e.g., measured and/or determined at or near the same times the PM count data and/or size distribution data was measured by the respective PM count devices 108). The reception component 502 can receive the new PM count data and new values (e.g., particle count, particle size distribution, particle composition, APH, APA and relative DC offset) for air samples measured by PM count devices 108 in real-time for processing by the PM monitoring server 102.

In addition, the PM monitoring server 102 can revise, update and optimize the one or more initial conversion models (e.g., via model update component 606) using the same or similar methods to those used to generate the one or more initial conversion models. For example, the PM monitoring server 102 can receive and use new reference PM count and/or size distribution data from the reference PM count devices 110 along with corresponding mass concentration data measured by the respectively paired monitor station devices 112 and values for conditional parameters associated with the reference PM count and/or size distribution data. The PM model update component 606 can continuously or periodically evaluate the new reference PM count and/or size distribution data to update and/or optimize the conversion models. For example, the model update component 606 can employ a conversion model to determine estimated mass concentration values based on new reference PM count/size distribution data and values for the one or more conditional parameters evaluated by the conversion model. The model update component 606 can compare the estimated mass concentration values with the actual mass concentration values determined by the monitor station device 112 to identify variances between the estimated mass concentration values and the actual mass concentration values. The model update component 606 can then perform root cause analysis over accumulated data to identify the causes for the variances and adjust the conversion model accordingly.

In some embodiments, the model generation component 506 generates different conversion models for different geographical areas and/or different pollution levels. In such embodiments, the PM monitoring server 102 can include model selection component 602 for selecting an appropriate conversion model to determine a PM mass concentration based on received or determined PM count and/or size distribution data and associated conditional information. For example, the model selection component 602 can identify or determine a geographical location associated with a PM count and/or size distribution measurement provided by a PM count device 108 and select the conversion model associated with that geographical location (e.g., based on the conversion model data 518). The model application component 604 can then employ the selected conversion model to determine a mass concentration value based on the PM count and/or size distribution data. In another example, the model selection component 602 can select identify or determine a relative DC offset value associated with a PM count and/or size distribution measurement provided by a PM count device 108 and select the conversion model associated with that relative DC offset value. For instance, in embodiments in which the PM monitoring server 102 determines a threshold DC offset value (e.g., using parameter extraction component 504 or model generation component 506), the model selection component 602 can determine whether the PM count and/or size distribution data can be associated with a high pollution state or a low pollution state based on the relative DC offset value being above or below the threshold DC offset value, respectively. The model selection component 602 can then select the appropriate conversion model (e.g., either the high pollution state conversion model or the low pollution state conversion model, respectively), for application by the model application component 604.

In some embodiments, the notification component 608 can generate and send notifications regarding mass concentration levels as determined by the model application component 604 (e.g., based on PM count and/or size distribution data provided by PM count devices 108 and/or reference PM count devices 110 using the one or more conversion models generated by the model generation component 506). In some embodiments, the notification component 608 can send notifications on a periodic basis, regardless of whether the mass concentration values are considered threatening or not. In other embodiments, the notification component 608 can generate and send notification regarding a current mass concentration level based on the mass concentration level exceeding a threshold level (e.g., indicating a high or critical PM mass concentration level). In other embodiments, the notification component 608 can generate and send a notification regarding a current PM mass concentration based on a determination that the average PM mass concentration level determined during a defined period of time (e.g., based on a plurality of measurements) exceeds a threshold level. For example, the notification component 608 can generate and send, via the one or more networks electronic notification to various entities, such as individuals at their respective user devices, (not shown) regarding current PM mass concentration levels. Such user devices can include but are not limited to phones, smartphones, desktop computers, laptop computers, wearable devices, televisions, Internet enabled televisions, and the like. Accordingly, in some embodiments, individuals can be notified in real-time regarding PM mass concentration levels in their environments and respond accordingly (e.g., by staying indoors when PM mass concentration levels are high and going outdoors only if and when PM mass concentration levels are low). In another example, the notification component 608 can also generate and send notifications to government agencies, regulatory agencies, emergency personnel and the like.

FIG. 7 illustrates a flow diagram of an example, non-limiting computer-implemented method 700 that facilitates monitoring PM mass concentration using relatively low cost devices in accordance with one or more embodiments of the present invention. Repetitive description of like elements employed in other embodiments of the present invention are omitted, for sake of brevity.

At 702, one or more components operatively coupled to a processor (e.g., PM monitoring server 102) determines relationships between first PM mass data, first PM count data and first conditional information. An example (without limitation) the first PM mass data comprises mass concentration data determined by a monitor station device (e.g., monitor station device 112$_1$) for a first atmospheric area over a first defined period of time. The first PM count data comprises reference PM count data determined by a reference PM count device (e.g., reference PM count device 110$_1$) for the first atmospheric area over the defined period of time. The first conditional information comprises first values for defined conditional parameters, wherein the first values are associated with the first atmospheric area over the period of time. At 704, the one or more components determine a conversion model based on the relationships. In some embodiments, the conversion model converts a PM count to a PM mass based on one or more conditional parameters of the defined conditional parameters (e.g., via model generation component 506).

Figure 8:
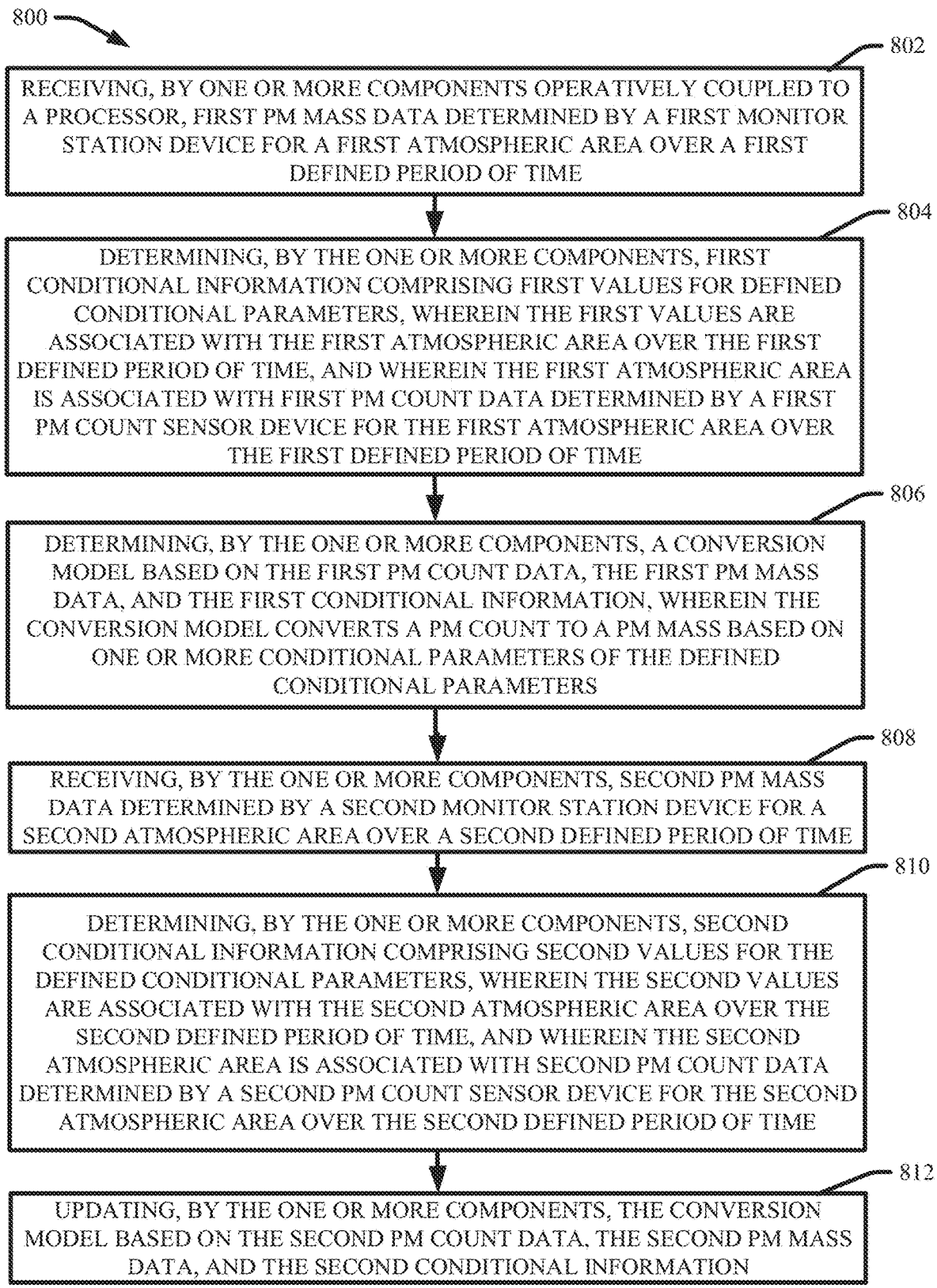
FIG. 8 illustrates a flow diagram of an example, non-limiting computer-implemented method that facilitates monitoring PM mass concentration using relatively low cost devices in accordance with one or more embodiments of the present invention.

FIG. 8 illustrates a flow diagram of an example, non-limiting computer-implemented method 800 that facilitates monitoring PM mass concentration using relatively low cost devices in accordance with one or more embodiments of the present invention. Repetitive description of like elements employed in other embodiments of the present invention is omitted for sake of brevity.

At 802 a one or more components operatively coupled to a processor (e.g., PM monitoring server 102) receive first PM mass data determined by a first monitor station device for a first atmospheric area over a first defined period of time. For example, the PM monitoring server 102 can receive PM mass concentration values for samples of air from the atmospheric area measured by the monitor station device at respective times (e.g., depending on the sampling rate, such as once every ten minutes, once an hour, etc.) over an initial sampling period (e.g., a week, a month, etc.). At 804, the one or more components determine first conditional information comprising first values for defined conditional parameters, wherein the first values are associated with the first atmospheric area over the first defined period of time, and wherein the first atmospheric area can be associated with first PM count data determined by a first PM count sensor device for the first atmospheric area over the first defined period of time (e.g., via the parameter extraction component 504).

For example, for each mass concentration measurement, the PM monitoring server 102 can determine or receive information regarding weather conditions associated with the atmospheric area at or near the time the mass concentration measurement was measured and at or near the location of the monitor station device. The PM monitoring server 102 can further associate each PM mass concentration measurement with reference PM data measured for a sample of air from the atmospheric area by a reference PM count device 110 at are near the same time as each PM mass concentration measurement, wherein the reference PM count device can be located at or near the same physical location as the monitor station device. The reference PM data can include at least a PM count and/or a PM size distribution for the sample. In some embodiments, the reference PM data can also include conditional information including the APH, the APA and the relative DC offset for the sample.

At 806, the one or more components determine a conversion model based on the first PM count data, the first PM mass data, and the first conditional information, wherein the conversion model converts a PM count to a PM mass based on one or more conditional parameters of the defined conditional parameters (e.g., via model generation component 506). The device can further employ the conversion model to convert PM count and/or size distribution measurements provided by other PM count device 108 to mass concentrations based on current conditional information associated with the PM count and/or size distribution measurements. At 806, the one or more components receive second PM mass data determined by a second monitor station device for a second atmospheric area over a second defined period of time (e.g., via reception component 502). At 810, the one or more components determine second conditional information comprising second values for the defined conditional parameters, wherein the second values are associated with the second atmospheric area over the second defined period of time, and wherein the second atmospheric area can be associated with second PM count data determined by a second PM count sensor device for the second atmospheric area over the second defined period of time. At 812, the one or more components update the conversion model based on the second PM count data, the second PM mass data, and the second conditional information (e.g., via model update component 606).

Figure 9:
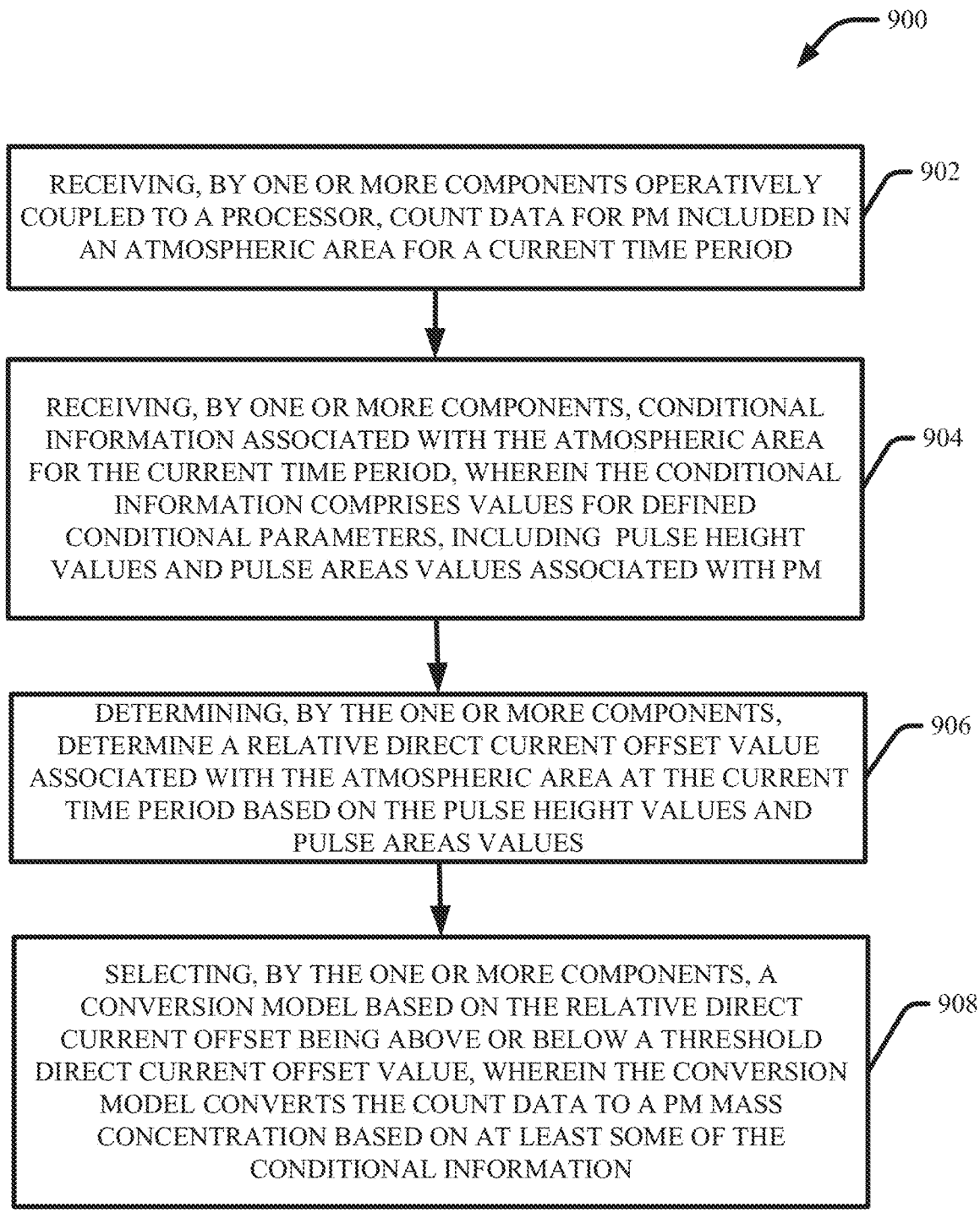
FIG. 9 illustrates a flow diagram of an example, non-limiting computer-implemented method that facilitates monitoring PM mass concentration using relatively low cost devices in accordance with one or more embodiments of the present invention.

FIG. 9 illustrates a flow diagram of an example, non-limiting computer-implemented method 900 that facilitates monitoring PM mass concentration using relatively low cost devices in accordance with one or more embodiments of the present invention. Repetitive description of like elements employed in other embodiments of the present invention is omitted for sake of brevity.

At 902 one or more components operatively coupled to a processor (e.g., PM monitoring server 102) receive count data for PM included in an atmospheric area for a current time period (e.g., via reception component 502). At 904, the one or more components receive conditional information associated with the atmospheric area for the current time period, wherein the conditional information comprises values for defined conditional parameters, including pulse height values and pulse areas values associated with PM (e.g., via reception component 502). At 906, the one or more components determine a relative direct current offset value associated with the atmospheric area at the current time period based on the pulse height values and pulse areas values (e.g., via model selection component 602). At 908, the one or more components select a conversion model based on the relative direct current offset being above or below a threshold direct current offset value (e.g., via model selection component 602), wherein the conversion model converts the count data to a PM mass concentration based on at least some of the conditional information. The device can further determine the PM mass concentration based on the count data using the conversion model.

Figure 10:
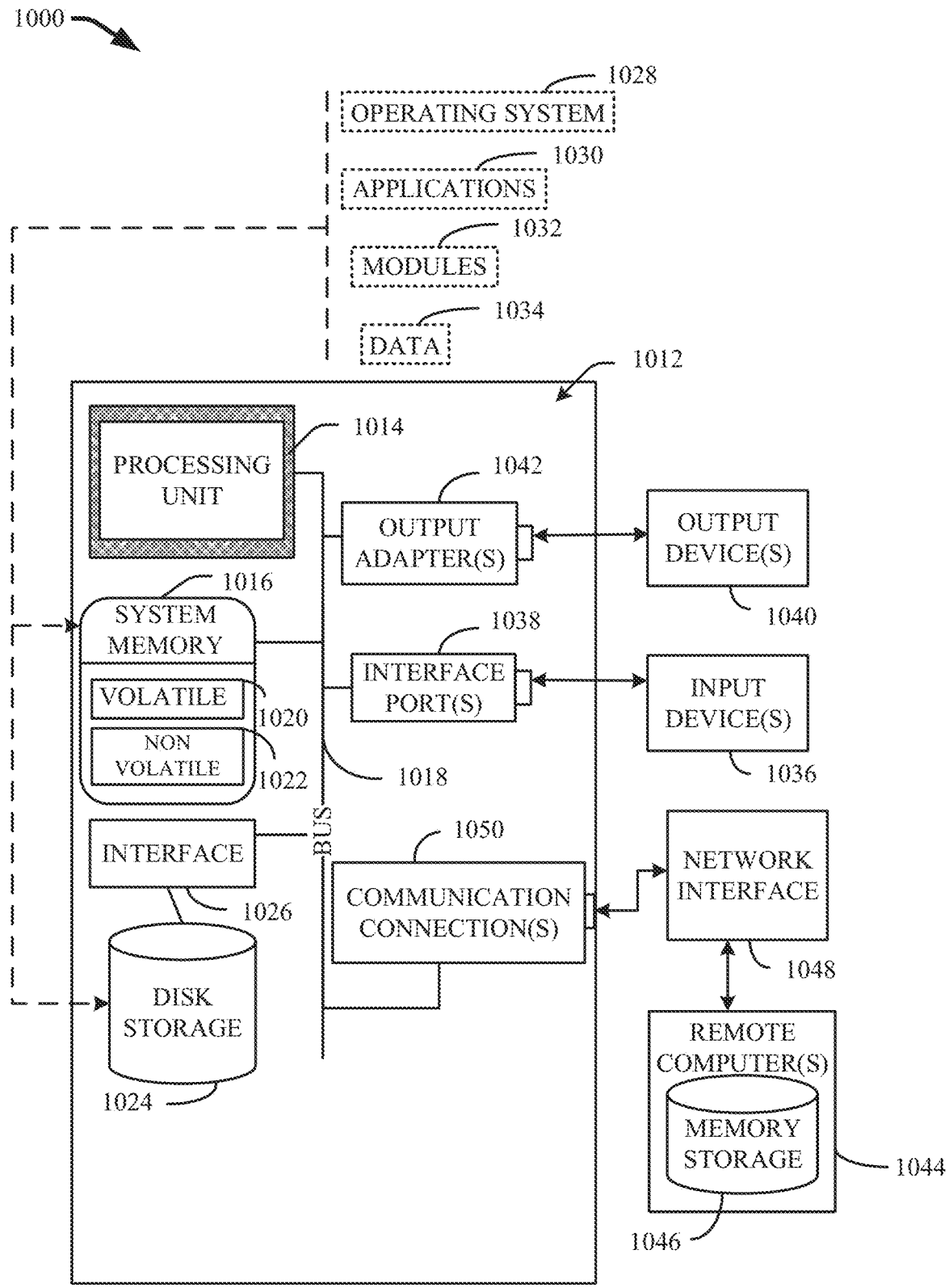
FIG. 10 illustrates a block diagram of an example non-limiting operating environment in accordance with one or more embodiments of the present invention.

FIG. 10 illustrates a block diagram of an example non-limiting operating environment in accordance with one or more embodiments of the present invention. As depicted, operating environment 1001 can include computer 1012. The computer 1012 can include a processing unit 1014, a memory 1016, and a bus 1018. The bus 1018 operably couples computer components including, but not limited to, the memory 1016 and processing unit 1014. The processing unit 1014 can be any of various available processors. Dual microprocessors and other multiprocessor architectures also can be employed as the processing unit 1014. The system bus 1018 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI). The system memory 1016 can also include volatile memory 1020 and nonvolatile memory 1022. The basic input/output system (BIOS), containing the basic routines to transfer information between elements within the computer 1012, such as during start-up, is stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/nonvolatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the bus 1018, a removable or non-removable interface is typically used, such as interface 1026. FIG. 10 also depicts software that acts as an intermediary between users and the basic computer resources described in the suitable operating environment 1001. Such software can also include, for example, an operating system 1028. Operating system 1028, which can be stored on disk storage 1024, acts to control and allocate resources of the computer 1012. System applications 1030 take advantage of the management of resources by operating system 1028 through program modules 1032 and program data 1034, e.g., stored either in system memory 1016 or on disk storage 1024. For example, the PM monitoring server 102 can be or include computer 1012 and one or more of the various components of the PM monitoring server (e.g., the reception component 502, the parameter extraction component 504, the model generation component 506, and/or the communication component 510) can be or include one or more applications 1030, and/or modules 1032. In another example, the communication component 510 of PM monitoring server 102 can be or include communication connections 1050. In another example, the processor 512 of the PM monitoring server 102 can be or include processing unit 1014 and the memory 514 of the PM monitoring server 102 can be or include system memory 1016 and/or disk storage 1024. It is to be appreciated that this disclosure can be implemented with various operating systems or combinations of operating systems.

In one or more embodiments, a user enters commands or information into the computer 1012 through input device(s) 1036. Input devices 1036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1014 through the system bus 1018 via interface port(s) 1038. Interface port(s) 1038 include, for example, a serial port, a parallel port, a game port, and a universal serial bus (USB). Output device(s) 1040 use some of the same type of ports as input device(s) 1036. Thus, for example, a USB port can be used to provide input to computer 1012, and to output information from computer 1012 to an output device 1040. Output adapter 1042 is provided to illustrate that there are some output devices 1040 like monitors, speakers, and printers, among other output devices 1040, which require special adapters. The output adapters 1042 include, by way of illustration and not limitation, video and sound cards that provide a means of connection between the output device 1040 and the system bus 1018. It should be noted that other devices and/or systems of devices provide both input and output capabilities such as remote computer(s) 1044.

Computer 1012 can operate in a networked environment using logical connections to one or more remote computers, such as remote computer(s) 1044. The remote computer(s) 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer(s) 1044. Remote computer(s) 1044 is logically connected to computer 1012 through a network interface 1048 and then physically connected via communication connection 1050. Network interface 1048 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

Embodiments of the present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
   determining, by one or more components operatively coupled to a processor, relationships between first particulate matter mass data and first particulate matter count data;
   determining, by the one or more components, a first conversion model based on relationships between a particulate matter count and a particulate matter mass, wherein the first conversion model converts the particulate matter count to the particulate matter mass based on one or more conditional parameters of defined conditional parameters; and
   evaluating, by the one or more components, second particulate matter mass data for a first atmospheric area, wherein the second particulate matter mass data is associated with second particulate matter count data determined by a reference particulate matter count device for the first atmospheric area over a second period of time, wherein the first conversion model or a second conversion model is selected based on a value of a relative direct current offset being above or below a threshold value of the relative direct current offset.

2. The computer-implemented method of claim 1, further comprising:
   receiving, by the one or more components, conditional information; and
   updating, by the one or more components, the first conversion model, in response to the receiving the conditional information.

3. The computer-implemented method of claim 1, wherein the defined conditional parameters are selected from a group consisting of accumulated pulse height, accumulated pulse area and the relative direct current offset.

4. The computer-implemented method of claim 1, wherein the defined conditional parameters are selected from a group consisting of: particle composition, size distribution, temperature, and humidity.

5. The computer-implemented method of claim 1, wherein the determining the first conversion model comprises employing machine learning.

6. The computer-implemented method of claim 1, further comprising:
   employing, by the one or more components, the first conversion model to determine a current particulate matter mass for the first atmospheric area based on second particulate matter count data determined for the first atmospheric area and second conditional information comprising second values for the one or more conditional parameters.

7. The computer-implemented method of claim 6, wherein the second values are associated with the first atmospheric area.

8. The computer-implemented method of claim 7, wherein the second particulate matter count data was determined by a particulate matter count device.

9. The computer-implemented method of claim 1, further comprising:
   receiving, by the one or more components, the second particulate matter mass data; and
   determining, by the one or more components, conditional information comprising values for the defined conditional parameters, wherein the values are associated with the first atmospheric area over the second period of time, and wherein the second particulate matter mass data is associated with second particulate matter count data determined by the reference particulate matter count device for the first atmospheric area over the second period of time.

10. The computer-implemented method of claim 9, further comprising:
    updating, by the one or more components, the first conversion model based on the second particulate matter count data, the second particulate matter mass data, and the conditional information.

11. The computer-implemented method of claim 1, wherein the reference particulate matter count device comprises a light scattering device, and wherein the first particulate matter mass data is determined by a monitor station device selected from a group consisting of: a tapered element oscillating microbalance device and a beta ray attenuation device.

12. A system, comprising:
    a memory;
    a processor operably coupled to the memory, wherein the processor:
    receives first particulate matter mass data and first particulate matter count data; and determines a first conversion model based on relationships between a particulate matter count and a particulate matter mass, wherein the first conversion model converts the particulate matter count to the particulate matter mass based on one or more conditional parameters of defined conditional parameter, wherein the system also evaluates second particulate matter mass data for a first atmospheric area, wherein the second particulate matter mass data is associated with second particulate matter count data determined by a reference particulate matter count device for the first atmospheric area over a second period of time wherein selected values comprise relative direct current offset values associated with a high pollution state based on a subset of relative direct current offset values respectively associated with a subset of particulate matter mass concentration levels within a threshold mass concentration level range.

13. The system of claim 12, wherein the defined conditional parameter comprises at least one of an accumulated pulse height or an accumulated pulse area.

14. The system of claim 12, wherein the defined conditional parameters comprise the relative direct current offset.

15. The system of claim 12, wherein the processor also:
selects the first conversion model or a second conversion model to employ in association with determining a current particulate matter mass for a first atmospheric area or a second atmospheric area based on second particulate matter count data for the first atmospheric area or the second atmospheric area and second conditional information for the first atmospheric area or the second atmospheric area.

16. The system of claim 15, wherein the second conditional information comprises second values for the defined conditional parameters associated with the first atmospheric area or the second atmospheric area at a current time, including a current relative direct current offset value, and wherein the model selection component selects the first conversion model or the second conversion model based on the current relative direct current offset value being above or below a threshold relative direct current offset value.

17. A computer program product for monitoring particulate matter mass concentration, the computer program product comprising a computer readable storage medium having program instructions embodied therewith, the program instructions executable by a processor to:
determine relationships between first particulate matter mass data and first particulate matter count data; and
create at least one conversion model based on the relationships, wherein the conversion model converts a particulate matter count to a particulate matter mass based on one or more conditional parameters of defined conditional parameters, wherein the at least one conversion model comprises a first conversion model associated with low pollution states based on a first subset of first conditional information associated with a first subset of particulate mass concentration levels below a threshold level and a second conversion model associated with high pollution states based on a second subset of the first conditional information associated with a second subset of the particulate mass concentration levels above the threshold level.

18. The computer program product of claim 17, wherein the program instructions are further executable by the processor to cause the processor to:
receive second particulate data, and second conditional information; and
update the conversion model in response to reception of the second particulate data, and the second conditional information.

19. The computer program product of claim 17, wherein the program instructions are further executable by the processor to cause the processor to:
receive second particulate matter mass data determined by a monitor station device for the first atmospheric area over a second period of time; and
determine second conditional information comprising second values for the defined conditional parameters, wherein the second values are associated with the first atmospheric area over the second period of time, and wherein the second particulate matter mass data is associated with second particulate matter count data determined by the reference particulate matter count device for the first atmospheric area over the second period of time.

* * * * *